United States Patent [19]
Nair et al.

[11] Patent Number: 6,150,408
[45] Date of Patent: Nov. 21, 2000

[54] TART CHERRY COMPOUNDS THAT HAVE ANTIOXIDANT ACTIVITY AND USES THEREOF

[75] Inventors: Muraleedharan G. Nair, Okemos, Mich.; Haibo Wang, Madera, Calif.; Gale M. Strasburg, East Lansing, Mich.; Alden M. Booren, Lansing, Mich.; James I. Gray, Haslett, Mich.

[73] Assignee: Board of Trustees operating Michigan State University, East Lansing, Mich.

[21] Appl. No.: 09/329,604

[22] Filed: Jun. 10, 1999

Related U.S. Application Data

[60] Provisional application No. 60/111,945, Dec. 11, 1998.

[51] Int. Cl.[7] .................. A61K 31/216; C07C 69/618; A23L 3/3463
[52] U.S. Cl. .................. 514/532; 560/75; 426/544
[58] Field of Search .................. 560/75; 514/532; 426/544

[56] References Cited

U.S. PATENT DOCUMENTS

| | | |
|---|---|---|
| 4,258,055 | 3/1981 | Lietti et al. . |
| 4,376,781 | 3/1983 | Lietti et al. . |
| 4,698,360 | 10/1987 | Masquelier . |
| 5,525,341 | 6/1996 | Walker et al. . |

OTHER PUBLICATIONS

Wang, H., et al., Journal of Agricultural and Food Chemistry, vol. 47, No. 3, pp. 840–844 (1999).
Kinsella, J.E., Food Technology, 85 Apr. 1993.
Wang, Haibo, et al., Journal of Natural Products, 62, No. 1, pp. 86–88 (1999).
Lietti, A., et al., Arzneimittel–Forschung, 26 (5) 829–832 (1976).
Chandra, A., et al., J. Agric. Food Chem. 41 No. 7 1062–1065 (1993).
Blazso, G., et al., Pharmazie 49 (7) 540–541 (1994).
Robak, J., et al., Polish Journal Pharmacology 48 (6) 555–564 (1996 Nov.–Dec.).
Ciulei, I., et al., AN. R. Acad. Farm 56(4), 531–537 (1990).
Gabor, M., et al., Acta Physiol Hung 77 (3–4) 197–208 (1991).
Gao, L., et al., Journal of Agricultural and Food Chemistry 43 (2) 343–346 (1995).
Moroney, M.A., J. Pharm Pharmacol 40(11):787–792 (Nov. 1988).

*Primary Examiner*—Gary Geist
*Assistant Examiner*—Leigh C. Maier
*Attorney, Agent, or Firm*—Ian C. McLeod

[57] ABSTRACT

Compounds that are isolatable from cherries and have antioxidant activity, and methods for isolating these compounds are described. In particular, the invention relates to 1-(3',4'-dihydroxycinnamoyl)-cyclopenta-2,3-diol and 1-(3',4'-dihydroxycinnamoyl)-cyclopenta-2,5-diol, which have antioxidant activity. These antioxidant compounds and compositions containing these compounds are useful as food preservatives, dietary supplements, nutraceuticals, and phytoceuticals.

25 Claims, 2 Drawing Sheets

TART CHERRY COMPOUNDS THAT HAVE ANTIOXIDANT ACTIVITY AND USES THEREOF

CROSS-REFERENCE TO RELATED APPLICATION

This application claims the benefit of U.S. Provisional Application Ser. No. 60/111,945 filed Dec. 11, 1998.

STATEMENT REGARDING FEDERALLY SPONSORED RESEARCH OR DEVELOPMENT

None.

BACKGROUND OF THE INVENTION (1) Field of the Invention

The present invention relates to novel compounds that are isolatable from cherries and have antioxidant activity and methods for isolating these compounds. In particular, the invention relates to 1-(3',4'-dihydroxycinnamoyl)-cyclopenta-2,3-diol and 1-(3',4'-dihydroxycinnamoyl)-cyclopenta-2,5-diol, which have antioxidant activity. These antioxidant compounds and compositions containing these compounds are useful as food preservatives, dietary supplements, nutraceuticals, and phytoceuticals.

(2) Description of Related Art

Many plant-derived compounds impart important positive or nutriceutical/phytoceutical traits to foods by way of their abilities to serve as cellular antioxidants by maintaining low levels of reactive oxygen intermediates, as anti-inflammatory agents by inhibiting prostaglandin synthesis, or as inhibitors of enzymes involved in cell proliferation. These activities may be important in ameliorating chronic diseases such as cancer, arthritis, and cardiovascular disease, which in some cases may be caused in part by free radicals (Kinsella et al. (1993). *Food Technol.* 47: 85–9).

Free radicals have been implicated in a number of pathological processes, which include aging, inflammation, reoxygenation of ischemic tissues, atherosclerosis, and various kinds of cancer (Halliwell et al. (1990). *Methods Enzymol.* 186: 1–88). The harmful activities of free radicals such as hydroxyl ($OH^-$) and peroxyl ($ROO^-$) radicals, and the superoxide anion ($O^-_2$) are constantly being produced as a result of metabolic reactions in living systems (Halliwell et al. ibid.). Living systems are protected from oxidative damage by these reactive species by enzymes such as superoxide dimutase and glutathione peroxidase, and by antioxidant compounds such as ascorbic acid, tocopherols, and carotenoids (Sies (1997). *Exp. Physiol.* 82: 291–5). However, when free radical production exceeds the antioxidant capacity of the organism, these free radicals attack lipids, proteins and DNA, thus damaging structural integrity and function of cell membranes, enzymes, and genetic material (Byers et al. (1992). *Ann. Rev. Nutr.* 12: 139–59). A growing body of evidence indicates that various pathological conditions such as cardiovascular disease, arthritis, various cancers, and Alzheimer's disease are associated, at least in part, with the damaging effects of uncontrolled free radical production (Byer et al. ibid.). It is also well known that lipids in meats are prone to oxidation, which contributes to rancidity in cooked and uncooked foods and natural lipid products for a variety of uses. It is also well known that cooking meats causes the formation of hetrocyclic aromatic amines (HAA) and other oxidative products. HAAs are dietary compounds that are formed naturally during cooking of muscle foods and are thought to arise from reactions involving creatine or creatinine, sugars, and amino acids. It has been shown that these HAAs are carcinogenic. Thus, compounds which would inhibit formation of HAAs during the cooking process would be particularly useful.

Many foods contain non-nutritive components such as flavanoids and other phenolic compounds which may provide protection against chronic disease through a multiplicity of effects which are still poorly understood (Tanaka et al. (1993). *Carcinogenesis* 14: 1321–5). These compounds may act as antioxidants by reacting with free radicals and thus interrupting the propagation of new free radical species, or by chelating metal ions such as $Fe_{2+}$ which catalyze lipid oxidation to alter their redox potentials. Therefore, naturally occurring antioxidants can be useful for treating various diseases. Thus, there is a need to identify antioxidative compounds from natural products. Since antioxidants may have ancillary effects, there is a need for novel antioxidant compounds which have beneficial effects not available with known antioxidants.

These natural antioxidant compounds could provide the food industry with natural compounds which would not only enhance food stability, but could also provide significant health benefits to the consumer. For example, antioxidants added to lipid containing products would extend the shelf life of these products. Antioxidant compounds would also be useful for the treatment of chronic diseases, either in prevention of disease, ameliorating the effects of disease, or stimulating the immune response to more effectively combat disease. There is evidence that has shown that some antioxidant supplements can significantly improve certain immune responses (Hertog et al. (1993). *Lancet* 342: 1007–11).

Finally, as the general population becomes older, the public interest in phytoceuticals as a means to inhibit chronic diseases and aging has steadily increased. The present invention addresses these interests by providing novel antioxidants which are effective at inhibiting oxidation, and can be isolated from natural sources in large quantities, easily and inexpensively.

SUMMARY OF THE INVENTION

The present invention provides a compound or a mixture of isomers of the compound, which is isolatable from tart cherries and in pure form has the formula:

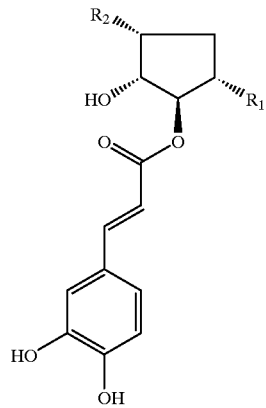

wherein $R_1$ and $R_2$ are selected from the group consisting of a hydroxyl and a hydrogen and in the compound one of the $R_1$ and $R_2$ is the hydroxyl. The present invention further provides 1-(3',4'-dihydroxycinnamoyl)-cyclopenta-2,5-diol and 1-(3',4'-dihydroxycinnamoyl)-cyclopenta-2,3-diol, which are isomers having antioxidant activity. The present invention also provides methods for using these antioxidants to inhibit oxidation of a material. These antioxidants are useful as anti-inflammatory compounds, anti-cancer compounds, food preservatives, dietary supplements, nutraceuticals, and phytoceuticals.

The present invention further relates to a consumable composition which comprises 1-(3',4'-dihydroxycinnamoyl)-cyclopenta-2,5-diol and 1-(3',4'-dihydroxycinnamoyl)-cyclopenta-2,3-diol either separately or a mixture thereof in admixture with a food grade carrier. The present invention further relates to a method for feeding a mammal the consumable composition which comprises 1-(3',4'-dihydroxycinnamoyl)-cyclopenta-2,5-diol and 1-(3', 4'-dihydroxycinnamoyl)-cyclopenta-2,3-diol either separately or a mixture thereof in admixture with a food grade carrier.

OBJECTS

It is therefore an object of the present invention to provide novel antioxidants such as 1-(3',4'-dihydroxycinnamoyl)-cyclopenta-2,5-diol and 1-(3',4'-dihydroxycinnamoyl)-cyclopenta-2,3-diol, which can be used in various materials prone to oxidation to prevent oxidation. In particular, it is an object to provide these compounds for use in anti-inflammatory compositions, anti-cancer compositions, food preservatives, dietary supplements, nutraceuticals, and phytonutrients. These and other objects will become increasingly apparent by reference to the following description and the drawings.

DETAILED DESCRIPTION OF THE INVENTION

Figure 1:
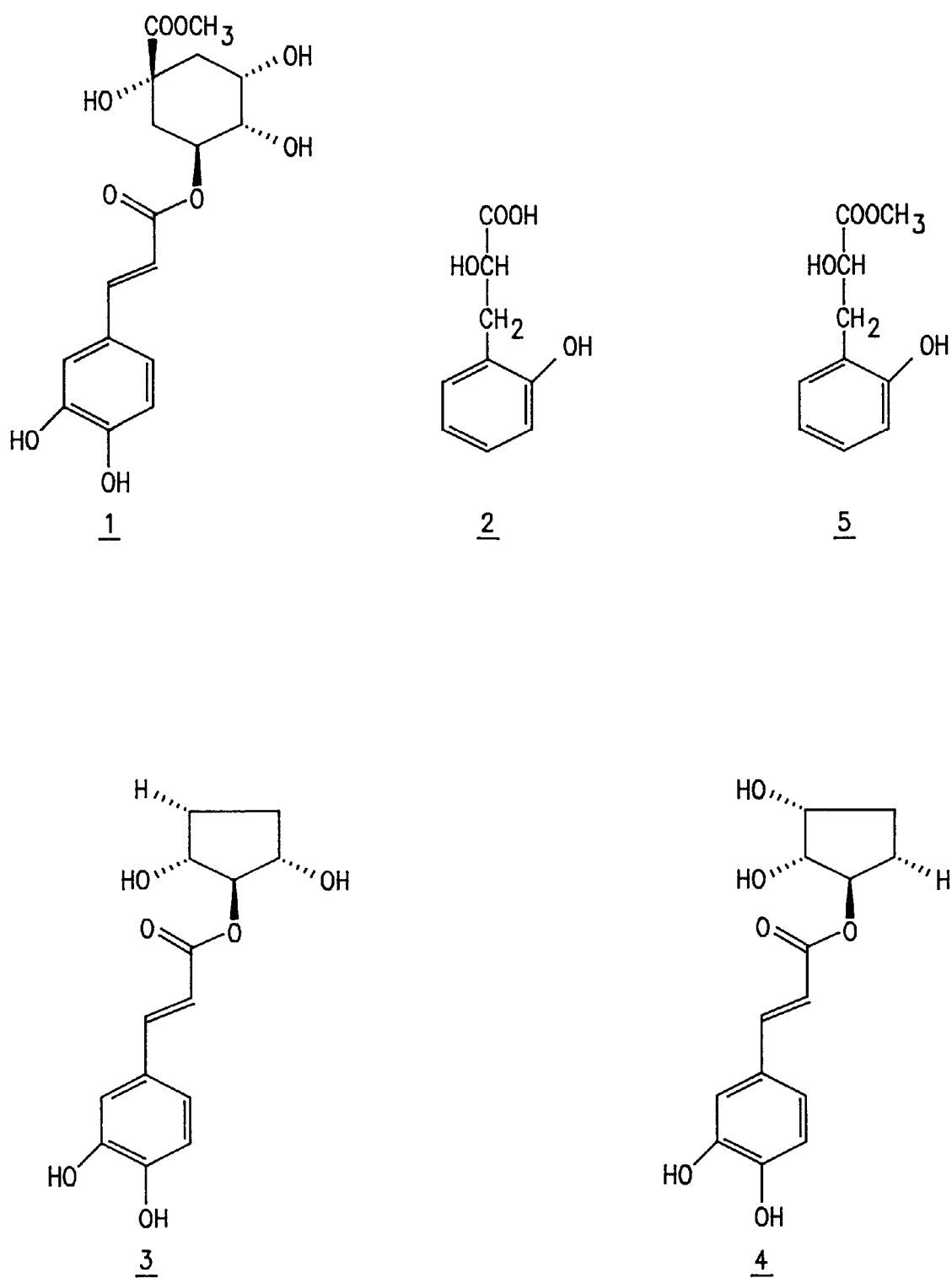
FIG. 1 shows the chemical structures for chlorogenic acid methyl ester (1), 2-hydroxy-3-(o-hydroxyphenyl)-propanoic acid (2), 1-(3',4'-dihydroxycinnamoyl)-cyclopenta-2,5-diol (3), 1-(3',4'-dihydroxycinnamoyl)-cyclopenta-2,3-diol (4), and 2-hydroxy-3-(o-hydroxyphenyl)-methylpropanol (5).

The present invention relates to a compound or a mixture of isomers isolatable from tart cherries and in pure form of the formula:

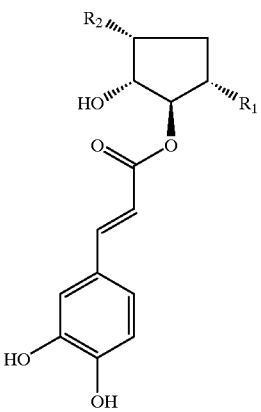

wherein $R_1$ and $R_2$ are selected from the group consisting of a hydroxyl and a hydrogen and one of the $R_1$ and $R_2$ is the hydroxyl. In particular, the invention relates to the isomer of the above compound wherein $R_1$ is hydroxyl and $R_2$ is hydrogen. This particular isomer of the compound is 1-(3', 4'-dihydroxycinnamoyl)-cyclopenta-2,5-diol, which is isolatable as a pure compound from tart cherries. The invention also relates to the isomer of the above compound wherein $R_1$ is hydrogen and $R_2$ is hydroxyl. This particular isomer of the compound is 1-(3',4'-dihydroxycinnamoyl)-cyclopenta-2,3-diol, which is isolatable as a pure compound from tart cherries.

The present invention also relates to a method of inhibiting oxidation in a material in need thereof which comprises providing a compound or a mixture of isomers isolatable from tart cherries and in pure form of the formula:

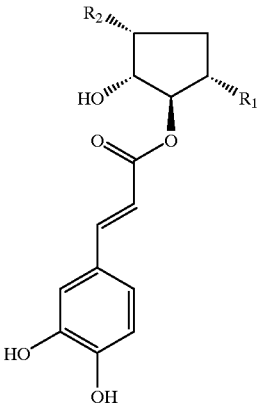

wherein $R_1$ and $R_2$ are selected from the group consisting of a hydroxyl or a hydrogen and one of the $R_1$ and $R_2$ is the hydroxyl with the material in an amount which inhibits oxidation of the material. In one embodiment, the method uses the isomer of the above compound wherein $R_1$ is hydroxyl and $R_2$ is hydrogen. This particular isomer of the compound is 1-(3',4'-dihydroxycinnamoyl)-cyclopenta-2,5-diol, which is isolatable from tart cherries and is used in an amount that inhibits the oxidation of the material. In another embodiment, the method uses the isomer of the above compound wherein $R_1$ is hydrogen and $R_2$ is hydroxyl. This particular isomer of the compound is 1-(3',4'-dihydroxycinnamoyl)-cyclopenta-2,3-diol, which is isolatable from tart cherries and is used in an amount that inhibits the oxidation of the material. In a further embodiment, the method uses a mixture of 1-(3',4'-dihydroxycinnamoyl)- cyclopenta-2,3-diol and 1-(3',4'-dihydroxycinnamoyl)-cyclopenta-2,5-diol in an amount which inhibits oxidation of the material.

The present invention also relates to a composition which comprises a compound isolatable from tart cherries and in pure form or as a mixture of isomers of the formula:

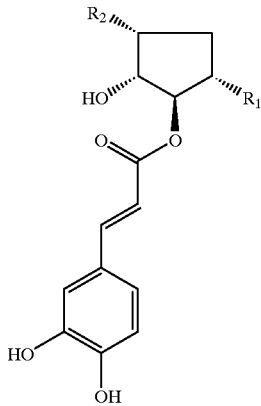

wherein $R_1$ and $R_2$ are selected from the group consisting of a hydroxyl or a hydrogen and one of the $R_1$ and $R_2$ is the hydroxyl; and a non-toxic carrier for the compound.

In one embodiment of the invention, the composition comprises 1-(3',4'-dihydroxycinnamoyl)-cyclopenta-2,3-diol as a pure compound or as a mixture with 1-(3',4'-dihydroxycinnamoyl)-cyclopenta-2,5-diol isolatable from tart cherries; and a non-toxic carrier or bulking agent for the compound. In another embodiment of the invention, the composition comprises 1-(3',4'-dihydroxycinnamoyl)-cyclopenta-2,5-diol as a pure compound or as a mixture with 1-(3',4'-dihydroxycinnamoyl)-cyclopenta-2,3-diol isolatable from tart cherries; and a non-toxic carrier or bulking agent for the compound. The composition can further contain other antioxidants such as anthocyanins, flavanoids, or other phenolics from cherries added to the pure compound. Furthermore, the carrier or bulking agent used in the compositions is a carrier suitable for animal or human use.

The term "carrier" or "bulking agent" is used to mean a composition which is used to hold the purified compounds of the present invention. These include any edible starch containing material or protein such as dried milk. Within this group are flour, sugar, soybean meal, malodextrin, and various condiments, such as salt, pepper, spices, and herbs. The bulking agent is used in an amount between $10^{-6}$ and $10^6$ parts by weight of the mixture.

The composition consists of the antioxidant of the present invention and a particulate edible bulking agent in an amount between about 0.1 to 30 parts per part of the invention, which product when introduced with an oxidizable material inhibits the oxidation of the material. The composition containing the antioxidant of the present invention can be tableted and used as a nutraceutical/dietary supplement. In general, the tablets provide a daily dose of the 1-(3',4'-dihydroxycinnamoyl)-cyclopenta-2,5-diol or 1-(3',4'-dihydroxycinnamoyl)-cyclopenta-2,3-diol as a pure compound, as an admixture containing both isomers, or as an admixture with other antioxidant compounds. The present invention either as a composition, mixture, or in purified form could be useful as an anti-inflammatory agent, or for the treatment of chronic diseases, either in prevention of disease, ameliorating the effects of disease, or stimulating the immune response to more effectively combat disease. In particular, the present invention either as a composition, mixture, or in purified form could be useful in preventing or treating various types of diseases which can in part or whole be caused by free radicals.

The composition of the present invention can further include one or more antioxidants selected from the group consisting of anthocyanins, cyanidins, bioflavanoids, phenolics and mixtures thereof. The anthocyanins, bioflavanoids and phenolics are preferably isolated from BALATON and MONTMORENCY cherries. That there are certain antioxidants found in cherries is in part shown in part by U.S. Pat. No. 5,985,636, in part in U.S. application Ser. No. 60/111,945, filed Dec. 11, 1998, and in part in U.S. application Ser. No. 09/317,310 filed May 24, 1999, all of which are herein incorporated by reference. In a preferred embodiment, the anthocyanin is selected from the group consisting of cyanidin-3-2"-O-β-D-glucopyranosyl-6"-O-α-L-rhamnosyl-β-D-glucopyranoside, cyanidin-3-6"-O-α-L-rhamnosyl-β-D-glucopyranoside, cyanidin-3-β-D-glucopyranoside, and mixtures thereof. In a preferred embodiment, the bioflavinoid is 7-methoxy-5,8,4'-trihydroxyflavone which was isolated in the manner described in Wang et al., J. Ag. And Food Chemistry 47 840–844 (1999).

The composition containing the antioxidant of the present invention, or the compound of the present invention can be added to food as a general antioxidant food additive. In particular, the food additive comprises 1-(3',4'-dihydroxycinnamoyl)-cyclopenta-2,5-diol or 1-(3',4'-dihydroxycinnamoyl)-cyclopenta-2,3-diol as a pure compound or as a mixture containing both isomers. The food additive can further include other antioxidants selected from the group consisting of anthocyanins, cyanidins, bioflavanoids, phenolics and mixtures thereof. In a preferred embodiment, the anthocyanin is selected from the group consisting of cyanidin-3-2"-O-β-D-glucopyranosyl-6"-O-α-L-rhamnosyl-β-D-glucopyranoside, cyanidin-3-6"-O-α-L-rhamnosyl-β-D-glucopyranoside, cyanidin-3-β-D-glucopyranoside, and mixtures thereof. In a preferred embodiment, the bioflavanoid is 7-methoxy-5,8,4'-trihydroxyflavone. The anthocyanins, bioflavanoids and phenolics are preferably isolated from BALATON and MONTMORENCY cherries. The composition containing the antioxidant of the present invention, or the compound of the present invention can be general antioxidant food additive that can be added to food which is either high (wet) or low moisture (dry), fresh or uncooked, cured or cooked. When added to food containing lipids, the antioxidant compounds or compositions inhibit oxidation of the lipids and thus inhibit the development of rancidity. The addition of the composition to meat prior to cooking inhibits the formation of heterocyclic aromatic amines (HAA), which occurs upon cooking and which have shown to be carcinogenic.

Compounds 1, 2, 3, and 4 were discovered by the inventors in ethyl acetate extracts of dried BALATON tart cherries, which had been further separated by medium pressure liquid chromatography (MPLC), preparative thin-layer chromatography (TLC) and high pressure liquid chromatography (HPLC). The structures for compounds 1, 2, 3, 4, and 5 are set forth in FIG. 1. Compounds 1, 3, and 4 were shown to have significant antioxidant activity. Compounds 3 and 4 were unknown prior to the discovery by the inventors and are the subject of the present invention. The identification of compounds 1, 2, and 5, and novel compounds 3 and 4 are set forth below.

Compound 1 was shown to be the known compound, chlorogenic acid methyl ester. Both the $^1H$ and $^{13}C$ nuclear magnetic resonance (NMR) spectral analysis of compound 1 revealed that the chemical shifts observed were identical to the published spectral data of chlorogenic acid methyl ester (Rumbero et al. (1991). *Phytochemistry* 30: 311–313).

Compound 2 was obtained from the cherry extract as a white solid, and was shown to be 2-hydroxy-3(o-hydroxyphenyl)-propanoic acid. Using fast atom bombardment-mass spectroscopy (FABMS), the molecular formula of compound 2 was determined to be $C_9H_{10}O_4$. The $^1H$ NMR spectrum revealed two aromatic protons that appeared as doublets at δ 7.40 and 6.86, respectively. Another two aromatic protons in the molecule appeared as triplets at δ 7.22 and 7.00, respectively. This indicated that there is an ortho-substituted aromatic moiety in the molecule. The multiplets at δ 4.19 and 2.80 were assigned to oxygenated methine and methylene moieties, respectively. The $^{13}C$ NMR spectrum of compound 2 supported the assignments determined by $^1H$ NMR, in addition to detecting a carbonyl carbon at δ 178.6. The structure of compound 2 was further confirmed by its conversion to compound 5 by methylation. Methylation of compound 2 by $CH_2N_2$ yielded one unit each of —$OCH_3$ and —$COOCH_3$. These data confirmed the presence of a phenolic OH and a COOH in compound 2. Therefore, the NMR confirmation of the identity of compound 2 as 2-hydroxy-3(o-hydroxyphenyl)-propanoic acid is in agreement with the methylation data. Circular dichroism (CD) studies of compound 2 showed that it was a racemic mixture as evident from the straight line in the CD spectrum. This is the first report showing that this compound occurred as a natural product.

Compound 3 of the present invention was obtained from the cherry extract as a pale yellow gum and was determined to be a previously unknown compound. The $^1H$ NMR spectrum of compound 3 indicated that two olefinic protons signals appeared as doublets at δ 7.45 and 6.19, respectively. A coupling constant of 15.9 Hz for these two protons suggested that they are in a trans orientation. The signals that appeared at δ 7.02, 6.97, and 6.75 were assigned to aromatic protons of a 3,4-dihydroxycinnamoyl group, respectively, and were similar to the chemical shifts of chlorogenic acid. The peaks at m/z 180 and 163 in the electron ionization mass spectra (EIMS) of compound 3 confirmed that it contained a caffeic acid moiety. The signals at δ 5.17, 3.82, and 3.54 were assigned to three oxygenated protons, one (δ 5.17) esterified, as well as multiplets at δ 1.83, integrating four protons of two methylene groups. These oxymethines appeared at 70.9 (x2) and 67.5, respectively, in the $^{13}C$ NMR spectrum. Compound 3 showed only one carbonyl carbon at 166.1 ppm. This fact that compound 3 had only one carbonyl carbon and no quartenary carbon around δ 70.9 suggested that the caffeic moiety was not connected to a quinic acid moiety, but to a cyclopentane-2,5-diol moiety. From these spectral data, the structure of compound 3 was assigned as 1-(3',4'-dihydroxycinnamoyl)-cyclopenta-2,5-diol. CD measurements did not show maxima or minima. This is because cyclopentane moieties do not absorb in the UV region. However, compound 3 gave observable peaks in their optical rotary dispersion (ORD) spectrum. Compound 3 is a novel compound which hitherto had been unknown to those skilled in the art.

Compound 4 of the present invention was obtained from the cherry extract as a colorless oily product and was determined to be a previously unknown compound. The $^1H$ NMR spectrum of compound 4 revealed a 3,4-dihydroxycinnamoyl moiety as was seen for compound 3. However, the two multiplets in compound 4, appearing at δ 2.15 and 1.95 were assigned to two methylene groups, respectively. The double quantum filter correlation spectroscopy (DQFCOSY) NMR experiment showed that the two $CH_2$ protons in compound 4 were correlated and adjacent to each other and also coupled to other hydrogens. The $^{13}C$ NMR spectrum of this compound revealed that there was only one carbonyl carbon, eight methine carbons, and two methylene carbons. Three of the methine carbons at δ 74.8, 73.0, and 68.3 were oxygenated and showed correlations to three methine protons at δ 3.64, 5.35, and 4.14, respectively, as evident from the heteronuclear multiple quantum correlation (HMQC) NMR spectrum. Also, five other methine carbons at δ 115.1, 116.5, 122.9, 146.8, and 115.8 showed correlations to three aromatic protons appearing at δ 7.04, 6.76, and 6.93 and two olefinic protons at 7.58 and 6.30 ppm, respectively. Based upon this data, compound 4 was assigned as 1-(3,4-dihydroxycinnamoyl)-cyclopenta-2,3-diol. CD measurements did not show maxima or minima. This is because cyclopentane moieties do not absorb in the UV region. However, compound 4 gave observable peaks in their ORD spectrum. Compound 4 is a novel compound which hitherto had been unknown to those skilled in the art.

Figure 2:
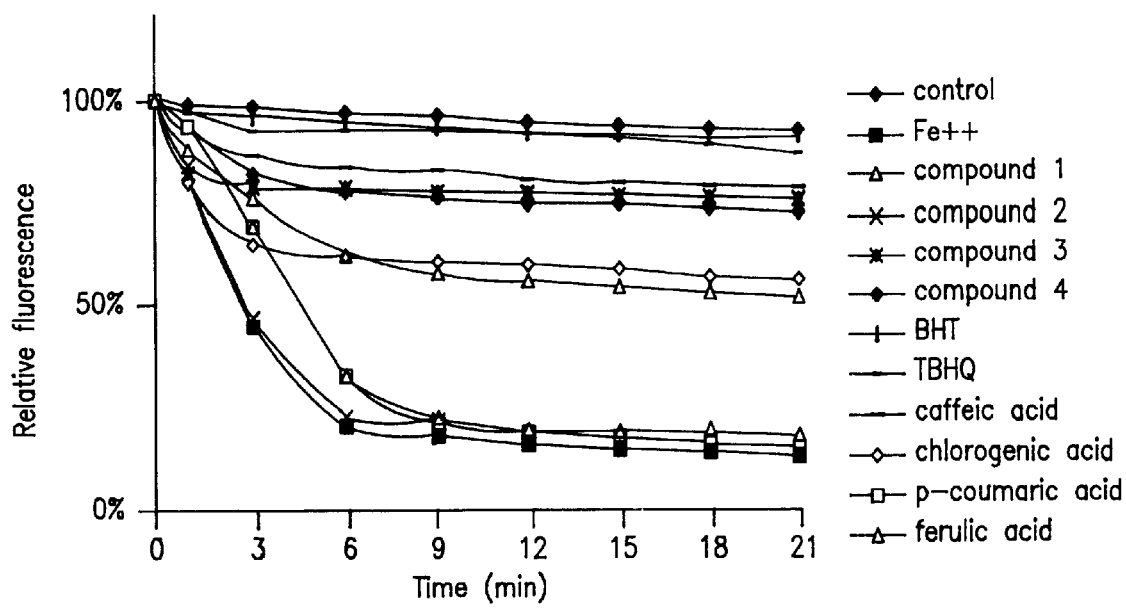
FIG. 2 shows the antioxidant activities of compounds 1, 3, and 4 and some commercial antioxidants at 20 $\mu$M concentration. The antioxidant activity of compound 2 was measured at 100 $\mu$M. The rate of peroxidation was monitored by a decrease in fluorescence intensity as a function of time. Relative intensity represents the fluorescence intensity at a given time divided by the initial intensity at the start of the assay. Values for each sample represent the mean for duplicate measurements.

The antioxidant activities of compounds 1, 2, 3, and 4 was determined by fluorescence spectroscopy in a $Fe^{2+}$-induced lipid peroxidation assay (Richman et al. (1996). *J. Chem. Soc.* 118: 11587–11591). The antioxidant activity for each compound was compared to caffeic acid, ferulic acid, chlorogenic acid, p-hydroxycinnamic acid, and the commercially available antioxidants, tert-butylhydroquinone (TBHQ) and butylated hydroxytoluene (BHT). The results of this assay is shown in FIG. 2. Each sample was tested at a concentration of 20 μM. In this assay, the lipid peroxidation was initiated by $Fe^{2+}$, and the rate of decrease in fluorescence intensity reflected the rate of lipid peroxidation. The inhibitory activities of $Fe^{2+}$-induced lipid peroxidation in the large unilamellar vesicles for compounds 3 and 4 were about 80% at 20 μM. Compound 1 showed about 50% inhibitory activity. However, compound 2 did not show any antioxidant activity even when tested at a 100 μM concentration. The assay results shown in FIG. 2 show that p-hydroxycinnamic acid is a weak antioxidant when compared to ferulic acid. However, the caffeic acid analogues, compounds 3 and 4, showed the highest antioxidant activity in the assay. The percent inhibition of lipid peroxidation for TBHQ and BHT were >90% at a 20 μM concentration (FIG. 2).

The variation in antioxidant activity among caffeoyl esters is dependent on the hydroxyl substitution of the aryl ring. More than one hydroxyl substitution in the aryl ring enhanced the antioxidant activity. Introduction of a second hydroxyl group in the ortho position, as in caffeic acid, also enhanced antioxidant activity. Methylation of the hydroxyl group in the ortho position of caffeic acid, as in ferulic acid, resulted in a decrease of antioxidant activity. This result is in agreement with published studies on the effects of hydroxycinnamates on the autoxidation of fats and lipids (Shihidi et al. (1992). *Crit. Rev. Food Sci. Nutr.* 32: 67–103; Cuvelier et al. (1992). *Biosci. Biotechnol. Biochem.* 56: 324–325). The results shown in FIG. 2, indicate that caffeic is the best antioxidant, and that compounds 4 and then 3 were next, followed by chlorogenic acid, and chlorogenic acid methyl ester (1). This trend in activity may be due to the difference in hydrophilicity or chelation properties of these compounds. Finally, the results shown in FIG. 2 show that the novel caffeic analogues, compounds 3 and 4, are at least comparable to the commercially available antioxidants BHT and TBHQ. Therefore, compounds 3 and 4 of the present invention are novel and effective antioxidants which are iosolatable from cherries. These compounds are useful for preventing unwanted oxidation of food products and as antioxidants useful for the prevention of diseases.

The following examples are intended to promote a further understanding of the present invention.

MATERIALS AND METHODS

Commercial antioxidants tert-butylhydroquinone (TBHQ) and butylated hydroxytoluene (BHT) were used as positive controls in the antioxidant assays. TBHQ was purchased from Eastman Chemical Products, Inc., Kingsport, Tenn. BHT was purchased from National Biochemicals Corporation, Cleveland, Ohio. Silica gel (60 mesh, 35–70 μm) used for the medium pressure liquid chromatography (MPLC) was purchased from E. Merck, Darmstadt, Germany. Thin-layer chromatography (TLC) plates were purchased from GF Uniplate, Analtech, Inc., Newark, Del. The TLC plates were viewed under 254 and 366 nm light sources after developing. For preparative high pressure liquid chromatography (HPLC) purification, two Jaigel-ODS, A-343-10 (20 mm×250 mm, 10 μm) columns (purchased from Dychrom, Santa Clara, Calif.) were used in tandem on the LC-20 purchased from Japan Analytical Industry Company, Tokyo, Japan. The peaks were identified using a model D-2500 Chromato-integrator (Hitachi, Tokyo, Japan) connected to a UV detector. $^1H$, $^{13}C$, double quantum filter correlation spectroscopy (DQFCOSY), and heteronuclear multiple quantum correlation (HMQC) NMR spectra were recorded on a Varian Unity 500 and Inova 300 MHZ spectrophotometers at 25° C. and referenced to the residual proton solvent resonance, $CD_3OD$ at 3.30 and 49.0 ppm and DMSO-$d_6$ at 2.49 and 39.5 ppm, for $^1H$ and $^{13}C$ NMR, respectively. Fast atom bombardment mass spectroscopy (FABMS) spectra Were produced using a glycerol matrix on a JEOL-AX110 and electron ionization mass spectroscopy (EIMS) spectra were obtained on a JOEL JMS-AX505 mass spectrometer. Circular dichroism (CD) and optical rotary dispersion (ORD) measurements were carried out using a JASCO J-710 CD-ORD spectropolarimeter (purchased from Japan Spectroscopic Company). For CD/ORD measurements, test compounds were dissolved in methanol (0.2 mg/mL), and CD/ORD were determined under the following conditions: scan mode (wavelength), bandwidth (0.5 nm), sensitivity (50 m degree), response (1 second), wavelength range (200–400 nm for CD and 200–800 for ORD), step resolution (1 nm), scan speed (200 nm/minute), and accumulation (1). Nitrogen (99.99%) was generated by a nitrogen generated model NG-150 at a rate of 15 L/minute. UV spectra of compounds in MeOH were measured on a Shimadzu UV-visible spectrophotometer (purchased from Shimadzu, Kyoto, Japan).

EXAMPLE 1

This example shows the preparation of extracts from tart cherries which were analyzed for antioxidant activity. The extracts obtained in this example were shown in subsequent Examples 2, 3, and 4 to contain either compound 1 and 2, 3, or 4, respectively.

Pitted and individually quick frozen BALATON cherries (*Prunus cerasus* L., Rosaceae), which were collected in July of 1995, were obtained from commercial growers in Traverse City, Mich. and supplied by the Cherry Marketing Institute, Inc. of Dewitt, Mich. Two kg of the tart cherries were lyophilized at 10° C., which yielded 342 g of freeze-dried cherries. The cherries (340 g) were milled and extracted with hexane (500 mL×3), EtOAc (500 mL×3), and MeOH (500 mL×3) to yield 0.71, 2.53, and 198.9 g of extract respectively.

The EtOAc extract (1.75 g) was fractionated by Si gel (100 g) MPLC using $CHCl_3$ and MeOH under gradient conditions, starting with 100% $CHCl_3$ and ending with 100% MeOH. Fractions 1–4 each had a volume of 125 mL and represented material that was eluted in approximately 100% $CHCl_3$. Fractions 5–8 each had a volume of 100 mL and represented material eluted from the column when the $CHCl_3$:MeOH was at a ratio of approximately 8:1. Fractions 9–12 each had a volume of 100 mL each and represented material eluted from the column when the $CHCl_3$:MeOH was at a ratio of approximately 4:1. Fractions 12–16 each had a volume of 150 mL and represented material eluted from the column in approximately 100% MeOH. The fractions were collected and combined after TLC analysis (Si gel plates developed with MeOH:$CHCl_3$ at a ratio of 16:1, for fractions 1–8; and MeOH:$CHCl_3$:HCOOH at a ratio of 1:4:0.2, for fractions 9–16) to yield fractions A–E consisting of 85, 134, 330, 910, and 225 mg respectively. Fractions A and B showed no antioxidant activity. Fractions C–E were further purified for antioxidant compounds as shown in Examples 2, 3, and 4.

EXAMPLE 2

This example shows the preparation of compounds 1 and 2 from fraction C of the cherry extract prepared in Example 1. These compounds were assayed in Example 6 for antioxidant activity.

Fraction C (250 mg) was purified by preparative silica TLC using MeOH:$CHCl_3$:HCOOH at a ratio of 4:1:0.2 as the mobile phase to yield 0.1 mg of compound 1 ($R_f$=0.50) and 8.9 mg compound 2 ($R_f$=0.67). The EIMS of compound 1 showed the molecular ion at m/z 386(10) and fragment ions at m/z 353 (8), 311 (5), 180 (3), 163 (5), and 83 (10). Also, the FABMS of compound 1 gave two peaks at m/z 391 (25 [M+Na]$^+$ and 369(3) [M+H]$^+$. $^1H$ and $^{13}C$ NMR spectra of compound 1 was identical to the published data of chlorogenic acid methyl ester (Rumero-Sanchez and Vazquez (1991). *Phytochemistry* 30: 311–313). The structure of compound 1 is shown in FIG. 1.

Compound 2 was a white solid. The analytical data for compound 2: IR(film) $v_{max}$ 3316, 1728, 1590, 1406 cm$^{-1}$; UV $\lambda_{max}$(MeOH) 218(3.04, 253 (3.42), 289 (3.66) nm; CD/ORD measurements gave straight lines indicating that compound 2 was obtained as a racemic mixture; $^1H$ NMR (CD$_3$OD) δ 7.40 (1 H, d, J=7.32 Hz, H-6'), 7.22 (1H, t, J=7.57 Hz, 7.32 Hz, H-4'), 7.00 (1H, t, J=7.57 Hz, 7.32 Hz, H-5'), 6.86 (1H, d, J=7.57 Hz, H-3'), 4.19 (1H, m, H-2), 2.80 (2H, m, H-3); $^{13}C$ NMR (DMSO-$d_6$): δ 178.6 (C-1), 141.6 (C-2'). 133.4 (C-6'), 128.4 (C-4'), 123.8 (C-5'), 121.3 (C-1'), 109.2 (C-3'), 73.4 (C-2), 48.6 (C-3); and FABMS, m/z 183 (4) [M+H]$^+$.

These data confirmed the identity of compound 2 as 2-hydroxy-3(o-hydroxyphenyl)-propanoic acid. The structure of compound 2 is shown in FIG. 1. Circular dichroism (CD) studies of compound 2 showed that it was a racemic mixture as evident from the straight line in the CD spectrum. This is the first report showing that this compound occurred as a natural product.

EXAMPLE 3

This example shows the preparation of compound 3 from fraction D of the cherry extract prepared in Example 1. Compound 3 was shown in Example 6 to have good antioxidant activity.

Fraction D (900 mg) was purified using a preparative HPLC with the mobile phase being MeOH:$H_2O$ at a ratio of 30:70. The flow rate was 3 mL per minute, which yielded 9.4 mg of compound 3 ($R_t$=58 minutes). Compound 3 was a pale yellow oily compound. The analytical data for compound 3: IR(film) $v_{max}$ 3351, 2926, 1669, 1599, 1379, 1267, 1076 cm$^{-1}$; UV $\lambda_{max}$(MeOH) 206(3.99), 215 (4.00), 243 (3.83, 299 (3.86), 325 (3.89) nm; ORD (m degree) 336 (75), 316 (−44), 298 (−40), 260 (35), 240 (−22) and 216 (52) nm; $^1H$ NMR (DMSO-$d_6$) δ 7.45 (1 H, d, J=15.9 Hz, H-7'), 7.01 (1H, d, J=1.8 Hz, H-2'), 6.96 (1H, dd, J=8.1 Hz, 1.8 Hz, H-6'), 6.75 (1H, d, J=8.1 Hz, H-5', 6.19 (1H, d, J=15.9 Hz, H-8'), 5.17 (1H, m, H-1), 3.82 (1H, m, H-2), 3.54 (1H, m, H-5), 1.83 (4H, m, H-3, H-4); $^{13}C$ NMR (DMSO-$d_6$): δ 166.1 (C-9'), 148.2 (C-3'). 145.5 (C-4'), 144.4 (C-7'), 125.7 (C-1'), 121.1 (C-6'), 115.8 (C-5'), 115.0 (C-8'), 114.6 (C-2'), 70.9 (C-2, C-5), 67.5 (C-1), 35.2 (C-3, C-4); and FABMS, m/z 281 (2) [M+H]$^+$; EIMS m/z 180 (93), 163 (100), 145 (20).

From these spectral data, the structure of compound 2 was assigned as 1-(3',4'-dihydroxycinnamoyl)-cyclopenta-2,5-diol. The structure of compound 3 is shown in FIG. 1. CD measurements did not show maxima or minima. This is because cyclopentane moieties do not absorb in the UV region. However, compound 3 gave observable peaks in their optical rotary dispersion (ORD) spectrum.

EXAMPLE 4

This example shows the preparation of compound 4 from fraction E of the cherry extract prepared in Example 1. Compound 4 was shown in Example 6 to have good antioxidant activity.

Fraction E (225 mg) was purified by preparative HPLC. The mobile phase was MeOH:H$_2$O at a ratio of 40:60, which was applied at a flow rate of 4 mL per minute. Subfractions 1 (180 mg), 2 (10.8 mg), 3 (8.4 mg), 4 (8 mg), and 5 (10 mg) were collected. Subfraction had no antioxidant activity and was found to contain malic acid, which was confirmed by its $^1$H NMR spectrum. Of the rest of the fractions, subfraction 2 was the most active and was subjected to an additional round of HPLC under the same conditions as above. The second round of HPLC yielded 9.4 mg of compound 4 ($R_f$=34 minutes). Compound 4 had an oily constitution. The analytical data for compound 4: IR(film) $v_{max}$ 3372, 1692, 1603, 1277, 1184, 1074 cm ; UV $\lambda_{max}$(MeOH) 203 (3.95), 215 (3.94), 243 (3.76), 299 (3.81) and 327 (3.90) nm; ORD (m degree) 314 (−58), 288 (−61) and 234 (−61) nm; $^1$H NMR (CD$_3$OD) δ 7.58 (1H, d, J=15.9 Hz, H-7'), 7.04 (1H, d, J=1.8 Hz, H-2'), 6.93 (1H, dd, J=8.2 Hz, 1.8 Hz, H-6'), 6.76 (1H, d, J=8.2 Hz, H-5'), 6.30 (1H, d, J=15.9 Hz, H-8'), 5.35 (1H, m, H-1), 4.14 (1H, m, H-3), 3.64 (1H, dd, J=8.3 Hz, 3.1 Hz, H-2), 2.15 (2H, m, H-4), 2.15 (2H, m, H-4), 2.15 (1H, m, H-5a), 1.95 (1H, m, H-5b); $^{13}$C NMR (CD$_3$OD): δ 169.0 (C-9'), 149.4 (C-3'). 146.8 (C-4'), 146.8 (C-7'), 128.0 (C-1'), 122.9 (C-6'), 116.5 (C-5'), 115.8 (C-8'), 115.1 (C-2'), 74.8 (C-2), 73.0 (C-1), 68.3 (C-2), 41.5 (C-5), 36.7 (C-4); FABMS, m/z 281 (2) [M+H]$^+$; EIMS m/z 180 (34), 163 (100).

From this data, compound 4 was assigned as 1-(3,4-dihydroxycinnamoyl)-cyclopenta-2,3-diol. The structure for compound 4 is shown in FIG. 1. Like compound 3, the CD measurements did not show maxima or minima. However, compound 4 gave observable peaks in their ORD spectrum. Compound 4 is a novel compound which heretofore had been unknown.

EXAMPLE 5

This example shows that methylation of compound 2 using N-nitroso-N-methyl urea produced compound 5. This example was performed to confirm that compound 2 was 2-hydroxy-3(o-hydroxyphenyl)-propanoic acid.

N-nitroso-N-methyl urea (1.5 g) was slowly added to a mixture of 100 mL of 25% KOH and 100 mL diethyl ether at 0° C. and allowed to react for about 1 hour. The yellow ether layer containing CH$_2$N$_2$ was separated using a separatory funnel (500 mL) and washed with cold water (100 mL) to remove excess KOH. Compound 2 (4 mg) was dissolved in methanol and mixed with excess CH$_2$N$_2$ reagent (5 mL) in ether. The reaction mixture was kept at room temperature for 1 hour. The solvent was then evaporated, which produced 4 mg of compound 5. Compound 5 was a white solid. The analytical data for compound 5: $^1$H NMR (CD$_3$OD) δ 7.35 (1H, d, J=7.32 Hz, H-6'), 7.25 (1H, dd, J=7.57 Hz, 7.32 Hz, H-4'), 7.01 (1H, dd, J=7.57 Hz, 7.32 Hz, H-5'), 6.87 (1H, d, J=7.57 Hz, H-3'), 4.49 (1H, dd, J=7.32 Hz, 4.88 Hz, H-2'), 2.80 (1H, d, J=12.45 Hz, 4.88 Hz, H-3a), 2.69 (1H, dd, J=12.45 Hz, 732 Hz, H-3b), 3.69 (3H, s, OCH$_3$), 3.47 (3H, s, COOCH$_3$). The structure for compound 5 is shown in FIG. 1.

EXAMPLE 6

This example compares the antioxidant activities of compounds 1, 2, 3, and 4 to various antioxidants. The antioxidants tested were caffeic acid, ferulic acid, chlorogenic acid, p-hydroxycinnamic acid, and the commercially available antioxidants, tert-butylhydroquinone (TBHQ) and butylated hydroxytoluene (BHT). This example used an Fe$^{2+}$-induced lipid peroxidation assay to detect antioxidant activity.

To prepare the substrate used in the Fe$^{2+}$-induced lipid peroxidation assay, a mixture containing 5 μmol of 1-stearoyl-2-linoleoyl-sn-glycerol-3-phosphocholine (obtained from Avanti Polar Lipids, Inc., Alabaster, Ala.) and 0.015 μmol of the fluorescence probe 3(p-(6-phenyl)-1,3,5-hexatrienyl)phenylpropionic acid (obtained from Molecular Probes, Inc., Eugene, Oreg.) was dried under vacuum using a rotary evaporator. The resulting lipid film was suspended in 500 μL of a solution containing 0.15 M NaCl, 0.1 mM EDTA, and 0.01 M 4-morpholinepropanesulfonic acid (MOPS) buffer. The MOPS buffer had been previously treated with CHELEX 100 (obtained from Sigma Chemicals, St. Louis, Mo.) at 5 g/100 mL buffer to remove any trace metal ions. The suspension was then subjected to 10 freeze-thaw cycles using a dry ice/ethanol bath. The lipid-buffer suspension was then extruded 29 times through a LIPOSO-FAST extruder (obtained from Avestin, Inc., Ottawa, Ontario, Canada) containing a polycarbonate membrane having a pore size of 100 nm to produce unilamellar liposomes.

To perform the Fe$^{2+}$-induced lipid peroxidation assay, a 20 μL aliquot of the above liposome suspension was diluted to 2 mL in CHELEX 100 treated buffer containing 200 mM NaCl, 100 mm N-2-hydroxyethylpiperazine-N'-2-ethanesulfonic acid (HEPES) buffer at pH 7.0, incubated for 5 minutes at room temperature, followed by incubation for another 5 minutes in the thermostatic cuvette holder of the spectrofluorometer which as held at 23° C. Peroxidation was then initiated by addition of 20 μL of 0.5 mM FeCl$_2$ to achieve a final concentration of 0.5 μM of Fe$^{2+}$ in the absence or presence of any of the test compounds. The control sample did not contain either Fe$^{2+}$ or any of the test compounds. Fluorescence intensity of these liposome solutions were measured every 3 minutes over a period of 21 minutes at an excitation wavelength of 384 nm using a fluorescence spectrofluorometer (SLM4800 obtained from SLM Instruments, Inc., Urbana, Ill.). The decrease in relative fluorescence intensity over time indicated the rate of peroxidation. The percent inhibition (PI) of the lipid oxidation was calculated using the equation:

$$PI = \{[(F_{rel})_{P1} - (F_{rel})_{Fe}]/[(F_{ref})_C - (F_{rel})_{Fe}]\} \times 100$$

where $(F_{rel})_{P1}$ is the relative fluorescence for the Fe(II) and test samples at the end of the 21 minute time period, $(F_{ref})_C$ is the relative fluorescence for the control sample at the end of the 21 minute time period, and $(F_{rel})_{Fe}$ is the relative fluorescence for the Fe(II)-containing sample at the end of the 21 minute time period (Arora et al. (1997). *J. Amer. Oil Chem. Soc.* 74: 1031–1040).

The results are shown in FIG. 2. The inhibitory activities of Fe$^{2+}$-induced lipid peroxidation in the large unilamellar vesicles for compounds 3 and 4 were about 80% at 20 μM. Compound 1 showed about 50% inhibitory activity. However, compound 2 did not show antioxidant activity even when tested at a 100 μM concentration. The assay results also showed that p-hydroxycinnamic acid was a weak antioxidant when compared to ferulic acid. However, the caffeic acid analogues, compounds 3 and 4, showed the highest antioxidant activity in this assay. The percent inhibition of lipid peroxidation for TBHQ and BHT were >90% at the 20 μM concentration. The assay showed that caffeic acid is the best oxidant, followed by compound 4, compound 3, chlorogenic acid, and chlorogenic acid methyl ester (1).

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

We claim:

1. An isolated compound or a mixture of isomers of the formula:

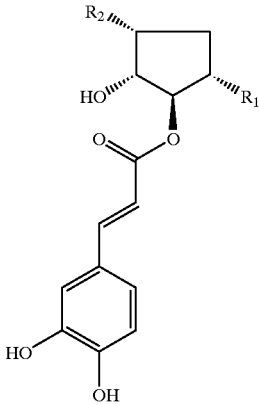

wherein $R_1$ and $R_2$ are selected from the group consisting of a hydroxyl and a hydrogen and one of $R_1$ and $R_2$ is hydroxyl.

2. The compound of claim 1 wherein $R_1$ is the hydroxyl and $R_2$ is the hydrogen.

3. The compound of claim 1 wherein $R_1$ is the hydrogen and $R_2$ is the hydroxyl.

4. Isolated 1-(3',4'-dihydroxycinnamoyl)-cyclopenta-2,3-diol.

5. Isolated 1-(3',4'-dihydroxylcinnamoyl)-cyclopenta-2,5-diol.

6. A composition which comprises:
(a) one or more isolated compounds of the formula:

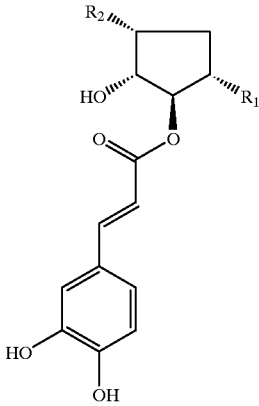

wherein $R_1$ and $R_2$ are selected from the group consisting of a hydroxyl or a hydrogen and one of $R_1$ and $R_2$ is the hydroxyl; and
(b) a non-toxic carrier for the compound.

7. A composition which comprises:
(a) isolated compound 1-(3',4'-dihydroxycinnamoyl)-cyclopenta-2,3-diol or as a mixture with an isolated 1-(3',4'-dihydroxylcinnamoyl)-cyclopenta-2,5-diol,; and (b) a non-toxic carrier for the compound.

8. A composition which comprises:
(a) isolated compound 1- (3',4'-dihydroxylcinnamoyl)-cyclopenta-2,5-diol or as a mixture with isolated compound 1-(3',4'-dihydroxycinnamoyl)-cyclopenta-2,3-diol,; and
(b) a non-toxic carrier for the compound.

9. The composition of claim 6 wherein the carrier is for human use.

10. The composition of any one of claims 6, 7 or 8 wherein the composition further comprises one or more antioxidants selected from the group consisting of anthocyanin, cyanidin, bioflavanoid, phenolic, and mixtures thereof.

11. The composition of claim 10 wherein the anthocyanin is from the group consisting of cyanidin-3-2"-O-β-D-glucopyranosyl-6"-O-α-L-rhamnosyl-β-D-glucopyranoside, cyanidin-3-6"-O-α-L-rhamnosyl-β-D-glucopyranoside cyanidin-3-β-D-glucopyranoside, and mixtures thereof.

12. The composition of claim 10 wherein the bioflavanoid is 7-methoxy-5,8,4'-trihydroxyflavone.

13. A method for inhibiting oxidation of an oxidizable material which comprises:
introducing with the material one or more isolated compounds of the formula:

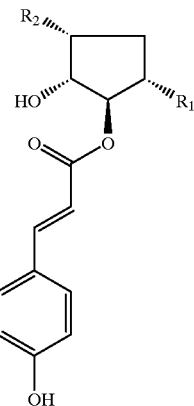

wherein $R_1$ and $R_2$ are selected from the group consisting of a hydroxyl and a hydrogen, and one of the $R_1$ and $R_2$ is the hydroxyl, in an amount, so that oxidation of the material is inhibited.

14. The method of claim 13 wherein $R_1$ is the hydroxyl and $R_2$ is the hydrogen.

15. The method of claim 13 wherein $R_1$ is the hydrogen and $R_2$ is the hydroxyl.

16. A method of inhibiting oxidation of an oxidizable material which comprises:
introducing with the material the isolated compound 1-(3',4'-dihydroxycinnamoyl)-cyclopenta-2,3-diol, in an amount, so that oxidation of the material is inhibited.

17. A method of inhibiting oxidation of a material which comprises:
introducing with the material a mixture of compound 1-(3',4'-dihydroxycinnamoyl)-cyclopenta-2,5-diol, in an amount, so that oxidation of the material is inhibited.

18. A method of inhibiting oxidation of an oxidizable material which comprises:
introducing with the material the isolated mixture of 1-(3',4'-dihydroxycinnamoyl)-cyclopenta-2,3-diol 1-(3',4'-dihydroxycinnamoyl) -cyclopenta 2,5-diol, in an amount, so that oxidation of the material is inhibited.

19. The method of claim 13 wherein the isolated compounds are from *Prunus cerasus*.

20. The method of claim 13 wherein the isolated compounds are from Balaton cherries.

21. The method of claim 13 wherein the isolated compounds are from Montmorency cherries.

22. The compound of claim 1 wherein the compound or a mixture of isomers is isolated from cherries (genus Prunus).

23. The compound of claim 1 wherein the compound or a mixture of isomers is isolated from tart cherries (*Prunus cerasus*).

24. The composition of claim 11 wherein the compound is isolated from cherries (genus Prunus).

25. The composition of claim 11 wherein the compound is isolated from tart cherries (*Prunus cerasus*).

* * * * *

UNITED STATES PATENT AND TRADEMARK OFFICE
CERTIFICATE OF CORRECTION

PATENT NO.    : 6,150,408                                  Page 1 of 1
DATED         : November 21, 2000
INVENTOR(S)   : Muraleedharan G. Nair, Haibo Wang, Gale M. Strasburg, Alden M. Booren and James I. Gray It is certified that error appears in the above-identified patent and that said Letters Patent is hereby corrected as shown below:

Column 1,
Line 28, "1074 cm" should be -- 1074 $cm^{-1}$ --.

Column 2,
Line 13, "$Fe_{2+}$" should be -- $Fe^{2+}$ --.

Column 11,
Line 4, "compound 2" should be -- compound 3 --.

Column 13,
Line 65 (Claim 7), "with an isolated" should be -- with isolated compound --.

Column 16,
Line 4 (Claim 24), "of Claim 11" should be -- of Claim 6 --.
Line 6 (Claim 25), "of Claim 11" should be -- of Claim 6 --.

Signed and Sealed this

Twenty-third Day of October, 2001

Attest:

NICHOLAS P. GODICI
Attesting Officer    Acting Director of the United States Patent and Trademark Office